United States Patent [19]

Nakanishi et al.

[11] 4,356,112
[45] Oct. 26, 1982

[54] CATALYST FOR PRODUCTION OF PHTHALIC ANHYDRIDE

[75] Inventors: Yoshiyuki Nakanishi; Yoji Akazawa; Noriaki Ikeda, all of Himeji; Takehiko Suzuki, Ohtsu, all of Japan

[73] Assignee: Nippon Shukubai Kagaku Kogyo Co. Ltd., Osaka, Japan

[21] Appl. No.: 210,689

[22] Filed: Nov. 26, 1980

[30] Foreign Application Priority Data

Dec. 3, 1979 [JP] Japan ................. 54-155608

[51] Int. Cl.$^3$ ............................................ B01J 27/14
[52] U.S. Cl. ..................................... 252/435; 252/437
[58] Field of Search ............................. 252/435, 437

[56] References Cited

U.S. PATENT DOCUMENTS

| | | | |
|---|---|---|---|
| 3,562,185 | 2/1971 | Friedrichsen et al. | 252/456 |
| 3,684,741 | 8/1972 | Friedrichsen et al. | 252/437 X |
| 3,870,655 | 3/1975 | Narba et al. | 252/437 X |
| 3,926,846 | 12/1975 | Ono et al. | 252/437 X |
| 4,046,780 | 9/1977 | Nakanishi et al. | 252/435 X |

FOREIGN PATENT DOCUMENTS

| | | | |
|---|---|---|---|
| 49-41036 | 11/1974 | Japan | 252/435 |
| 52-4538 | 9/1977 | Japan . | |
| 53-146459 | 12/1978 | Japan . | |

Primary Examiner—Delbert E. Gantz
Assistant Examiner—William G. Wright
Attorney, Agent, or Firm—Sherman & Shalloway

[57] ABSTRACT

A catalyst for the production of phthalic anhydride by the catalytic vapor-phase oxidation of o-xylene or naphthalene with molecular oxygen, said catalyst comprising a catalytically active material composed of 1 to 20 parts by weight of $V_2O_5$ of vanadium oxide and 99 to 80 parts by weight as $TiO_2$ of anatase-type titanium oxide being porous and having a particle diameter substantially of 0.4 to 0.7 micron and a specific surface area of 10 to 60 m$^2$/g, and per 100 parts by weight of the sum of these two components, 0.01 to 1 part by weight as $Nb_2O_5$ of niobium, 0.05 to 1.2 parts by weight as oxide of potassium, cesium, rubidium or thallium, 0.2 to 1.2 parts by weight as $P_2O_5$ of phosphorus and 0.5 to 10 parts by weight as $Sb_2O_3$ of antimony, said catalytically active material being supported on a porous carrier in an amount of 3 to 200 g/100 cc of carrier.

5 Claims, No Drawings

CATALYST FOR PRODUCTION OF PHTHALIC ANHYDRIDE

This invention relates to a catalyst suitable for producing phthalic anhydride by the catalytic vapor-phase oxidation of o-xylene or naphthalene with a gas containing molecular oxygen. More specifically, it relates to a catalyst which contains vanadium oxide and titanium oxide as catalytically active materials supported on an inert carrier and is useful for the stable industrial production of phthalic anhydride by the catalytic vapor-phase oxidation of a starting gas containing o-xylene or naphthalene in a high concentration with a molecular oxygen-containing gas.

Catalysts suitable for the production of phthalic anhydride, which mainly contain vanadium oxide and titanium oxide as a catalytically active material supported on an inert carrier have been well known, and reported, for example, in U.S. Pat. Nos. 3,562,185, 3,926,846 and 4,046,780 and Japanese Laid-Open Patent Publications Nos. 89694/74 (German Pat. No. 2260615) and 5661/72 (German Pat. No. 2142838). Some of these known catalysts have been industrially used with good results. Particularly, the present inventors have ascertained that the catalysts disclosed in Japanese Patent Publications Nos. 41036/74 and 4538/77 are very effective in industrial operations because of their high performance level and durability.

Phthalic anhydride has been produced previously by the catalytic vapor-phase oxidation of o-xylene or naphthalene using air as an oxidizer. To avoid the danger of explosion, it is usual in most cases to maintain the concentration of the starting gas below the lower limit of explosive range during the reaction. With technological advances made in the selectivity and heat durability of the catalyst and in reaction engineering, operations within an explosive range have been attempted for the past several years to increase productivity per unit converter and save energy. According to these operations, the concentration of naphthalene or o-xylene in the air is increased to more than the lower limit of explosive range (40 g/NM$^3$-air) in the aforesaid catalytic vapor-phase oxidation process. Suggestions relating to such a process are disclosed in Japanese Laid-Open Patent Publications Nos. 40539/75 (West German Laid-Open Publication No. 2,417,145), 40514/75 (West German Laid-Open Publication No. 2,330,841), and 134618/74 (West German Laid-Open Publication No. 2,309,657).

These patent documents show that, for example, o-xylene can be used in a concentration of as high as 40 to 60 g/NM$^3$ whereas a level of below 40 g of o-xylene/NM$^3$ was previously required. One reason for this is presumably that the danger of explosion can be avoided by keeping the composition of the product gas from the outlet of the converter outside the explosive range. By increasing the linear velocity of the gas between the material charging section and the catalyst layer in the converter, the danger of explosion can be avoided at a gas concentration of up to a certain point even if the gas composition in the stationary state is within the explosive range. After the gas has left the gas outlet of the converter, however, it is impossible, in view of the operation of recovering the resulting phthalic anhydride, to narrow the apparent explosive range of the gas composition by increasing the linear velocity of the gas. Accordingly, as the operating condition of the aforesaid oxidation reaction in an explosive range, the gas concentration of o-xylene or naphthalene in air was previously regarded as up to about 60 g/NM$^3$.

Various restrictions, however, are imposed on the performance of catalysts used in such a reaction in a high gas concentration. The catalytic vapor-phase oxidation of naphthalene or o-xylene to form phthalic anhydride is very exothermic. When the concentration of the gas is increased, unusually high heat is liable to be generated locally in the catalyst layer (such a locality is generally known in the art as a "hot spot"). This induces excessive oxidation reaction, which results in a decrease in the yield of phthalic anhydride and in a marked degradation of the catalyst at the hot spot. It was found that this decrease in yield occurs remarkably in a gas concentration of about 60 g/NM$^3$ even with a conventional catalyst which maintains a high very high level of catalytic performance in a gas concentration of below 40 g/NM$^3$. In a higher concentration such as 80 g/NM$^3$, the temperature of the hot spot exceeds 500° C., and side-reactions to form maleic anhydride, benzoic acid, carbon dioxide, etc. increase.

There was also an attempt to cope with this high concentration reaction by adding steam to the starting gas (the steam is mostly obtained from the reaction product gas as recycled steam) so as to raise the lower limit of explosion and widen the safe range and also to repress the increase of temperature of the hot spot. The effect brought about by the repression of the increase of the temperature of the hot spot is described in Japanese Laid-Open Patent Publication No. 40514/75.

It has been found difficult however to adapt a known conventional catalyst to such a new reaction condition. Surely, the catalyst keeps the expected productivity of phthalic anhydride for some time after the starting of the reaction, but it gradually loses its catalytic activity and becomes useless in industrial practice.

Some of the present inventors have proposed a suitable catalyst for the production of phthalic anhydride which has good durability in such a high concentration reaction (see, Japanese Patent Application No. 146459/78). The present inventors have now found that by adding antimony as an additional element to this catalyst, its heat stability, steam resistance and selectivity for phthalic anhydride can be improved to provide a catalyst for production of phthalic anhydride which well withstands use for an extended period of time.

Thus, according to this invention there is provided a catalyst for the production of phthalic anhydride by the catalytic vapor-phase oxidation of o-xylene or naphthalene with molecular oxygen, said catalyst comprising a catalytically active material composed of 1 to 20 parts by weight as V$_2$O$_5$ vanadium oxide, 99 to 80 parts by weight as TiO$_2$ of anatase-type titanium oxide being porous and having a particle diameter substantially of 0.4 to 0.7 micron and a specific surface area of 10 to 60 m$^2$/g, and per 100 parts by weight of the sum of these two components, 0.01 to 1 part by weight as Nb$_2$O$_5$ of niobium, 0.05 to 1.2 parts by weight as an oxide of potassium, cesium, rubidium or thallium, 0.2 to 1.2 parts by weight as P$_2$O$_5$ of phosphorus and 0.5 to 10 parts by weight as Sb$_2$O$_3$ of antimony, said catalytically active material being supported on a porous carrier in an amount of 3 to 200 g/100 cc of carrier.

The greatest feature of the present invention is the use of porous anatase-type TiO$_2$ having a particle diameter of 0.4 to 0.7 micron, preferably 0.45 to 0.60 micron and a specific surface area of 10 to 60 m$^2$/g, preferably 15 to 40 m$^2$/g as a TiO$_2$ source in the catalytically active material. This porous anatase-type $TiO_2$ can be produced by the so-called "solution method" and cannot be crushed by a mechanical means such as a hammer mill. As far as this is concerned, this $TiO_2$ has such a strength as can be regarded as "primary particles".

Anatase-type $TiO_2$ having the unique property of possessing a high specific surface area despite its large particle diameter is produced by mixing ilmenite ($FeOTiO_2$) with sulfuric acid of lower concentration (usually 70 to 80%) than in the solid method, blowing heated steam at about 150° C. into the aqueous solution to hydrolyze it, and calcining the hydrous precipitate.

The porous carrier of the present invention has an alumina content of not more than 10% by weight, preferably not more than 5% by weight, a silicon carbide content of at least 80% by weight, preferably at least 95% by weight, and an apparent porosity (to be referred to simply as "porosity" hereinbelow) of at least 10%, preferably 15 to 45%. A typical example of the carrier is the one obtained by self-bonding of a powder of SiC having a purity of 98% to adjust its porosity to 15–40%. The shape of the carrier is not particularly limited so long as its size is 2 to 15 mm in diameter. Spherical or circular-cylindrical carriers are suitable for handling.

The catalytically active material is supported on the carrier by a known conventional method. The simplest method comprises placing a fixed amount of the carrier in a rotary drum adapted to be externally heated, and spraying a liquid (e.g., slurry) containing the catalytically active material onto the carrier while maintaining the temperature at 200° to 300° C. The suitable amount of the catalytic material supported is 3 to 200 g/100 cc of carrier although varying depending upon the size of the carrier.

In order for the catalyst of this invention to meet the above described requirements that the total volume of pores having a diameter of 0.15 to 0.45 micron present in the layer of the catalytically active material on the carrier is at least 50%, preferably at least 75%, of that of pores having a diameter of not more than 10 microns present in said layer of the catalytically active material, it is necessary to adjust the slurry concentration according to the particle diameter of the primary particles of titanium oxide, as described in the specification of Japanese Patent Publication No. 41036/74 (U.S. Pat. No. 3,926,846).

The titanium oxide used in the catalyst of this invention is composed of substantially porous particles of a diameter of 0.4 to 0.7 micron and of a high specific surface area of 10 to 60 $m^2/g$ which are essentially aggregated masses of primary particles.

The particle diameter of the primary particles can be measured by a mercury penetration-type porosimeter. When using porous titanium oxide consisting of primary particles having a particle diameter in the range of 0.005 to 0.05 micron, the concentration of the slurry is 5 to 25% by weight, preferably 10 to 20% by weight. When using porous titanium oxide consisting of primary particles having a particle diameter of 0.05 to 0.4 micron, the slurry concentration is 10 to 40% by weight, preferably 15 to 25% by weight.

The catalyst so obtained is then calcined at 300° to 600° C., preferably 350° to 550° C., for 2 to 10 hours in a current of air.

Depending upon the raw ore, $TiO_2$ may include iron, zinc, aluminum, manganese, chromium, calcium, lead, etc. These incidental elements are not detrimental to the reaction if their total amount is less than 0.5% by weight based on $TiO_2$.

Raw materials for $V_2O_5$, $Nb_2O_5$, $P_2O_5$, $K_2O$, $Cs_2O$, $Rb_2O$ and $Tl_2O$ can be suitably selected from those which can change to oxides upon heating, such as the sulfates, ammonium salts, nitrates, organic acid salts, halides, and hydroxides of these metals.

Suitable raw materials for antimony to be added to the catalytically active material according to the present invention are antimony trioxide ($Sb_2O_3$) or any compounds of antimony capable of forming its oxides by calcination. More specifically, antimony vanadium oxide ($SbVO_4$) prepared by reacting a vanadium compound and an antimony compound can be used with successful results.

The catalyst in accordance with this invention is suitable for the catalytic oxidation of o-xylene or naphthalene, preferably o-xylene, to form phthalic anhydride.

In use, the catalyst obtained is packed into a tube having an inside diameter of 15 to 40 mm, preferably 15 to 27 mm, and a length of 1 to 5 meters, preferably 1.5 to 3 meters, and being kept at a temperature of 250° to 400° C., preferably 270° to 380° C. by a heat transfer medium. Through this catalyst layer, o-xylene or naphthalene, the starting material, is passed together with air or an oxygen-containing gas composed of 5 to 21% by volume of oxygen in a concentration of 5 to 60 g-raw material/$NM^3$-air or 5 to 110 g-raw material/$NM^3$-molecular oxygen containing gas, at a space velocity (to be abbreviated S.V.) of 1000 to 6000 $hr^{-1}$ (STP), preferably 1000 to 4000 $hr^{-1}$ (STP).

In a particularly advantageous embodiment of using the catalyst of this invention, the oxidation reaction of o-xylene or naphthalene is carried out under the conditions mentioned above by controlling the activity of the catalyst along the flowing of the gas from the inlet to the outlet of the tube.

In a specific embodiment, a stacked catalyst layer composed of a layer of a "first-stage catalyst" and a layer of a "second-stage catalyst" is used. The first-stage catalyst comprises a catalytically active material composed of 1 to 20 parts by weight of $V_2O_5$ and 99 to 80 parts by weight of anatase-type $TiO_2$ having the physical properties mentioned above, and per 100 parts by weight of the sum of these two components, 0.01 to 1 part by weight of $Nb_2O_5$, 0.05 to 1.2 parts by weight of at least one ingredient selected from $K_2O$, $Cs_2O$, $Rb_2O$ and $Tl_2O$, 0.2 to 0.4 part by weight of $P_2O_5$ and 0.5 to 10 parts by weight of $Sb_2O_3$, and a carrier having an alumina content of not more than 10% by weight, preferably not more than 5% by weight, a silicon carbide content of at least 80% by weight, preferably at least 95% by weight and an apparent porosity of at least 10% and supporting the above catalytically active material thereon. This first-stage catalyst occupies 30 to 70% of the total height of the catalyst layer in the reaction tube from the inlet for the starting gas. The second-stage catalyst having a higher catalytic activity than the first-stage catalyst and the same composition as the first-stage catalyst except that the amount of $P_2O_5$ was changed to 0.4 to 1.2 parts by weight occupies the remainder (70 to 30% from the gas outlet portion) of the height of the catalyst layer. If desired, the catalyst may be packed in three or more layers. In this case, the $P_2O_5$ content of the catalyst needs to be increased stepwise from the gas inlet portion to the gas outlet portion of the catalyst layer so that the aforesaid requirement of $P_2O_5$ content in the first-stage and second-stage catalysts is met.

By using such a stacked catalyst, the increase of the temperature of the hot spot in the catalyst layer is markedly inhibited.

In particular, the loadability and durability of the catalyst are markedly improved. For example, even when o-xylene is oxidized under severe conditions involving using a gas containing molecular oxygen with an oxygen content of about 10% by volume and passing the ortho-xylene in a concentration of more than 80 g/NM$^3$ of the molecular oxygen-containing gas, phthalic anhydride can be obtained in a high yield of more than 112% by weight stably over a long period of time.

Advantageously, the present invention also provides a method for controlling the catalytic activity of an antimony-added $V_2O_5$-$TiO_2$ type supported catalyst so as to utilize its excellent characteristics. Specifically, by increasing the amount of the catalytically active substances to be supported on the carrier to 15 to 200 g/100 cc of carrier, the reaction temperature can be decreased to below 350° C., preferably below 330° C. and consequently, the catalyst exhibits excellent selectivity. Moreover, by including 0.5 to 10 parts by weight of $Sb_2O_3$ as Sb per 100 parts by weight of the sum of $V_2O_5$ and $TiO_2$, the selectivity of the catalyst is increased and its activity can be easily controlled. Specifically, according to this method, the reaction is carried out by using a stacked catalyst consisting of a first-stage catalyst which is packed in a height corresponding to 30 to 70% of the total height of the catalyst layer from the gas inlet and is composed of a catalytically active material consisting of 1 to 20 parts by weight of $V_2O_5$ and 99 to 80 parts by weight of anatase-type $TiO_2$ having the aforesaid properties and per 100 parts by weight of the sum of these two components, 0.01 to 1 part by weight of $Nb_2O_5$, 0.2 to 1.2 parts by weight of $P_2O_5$, 0.05 to 1.2 parts by weight of at least one component selected from the group consisting of $K_2O$, $Cs_2O$, $Rb_2O$ and $Al_2O$ and 2 to 10 parts by weight of $Sb_2O_3$, the catalytically active material being supported on a porous carrier composed of not more than 10% by weight, preferably not more than 5% by weight, of an aluminum compound as $Al_2O_3$ and at least 80% by weight, preferably at least 95% by weight, of SiC, and a second-stage catalyst packed in the remaining 70 to 30% of the height of the catalyst layer on the gas outlet side and having higher activity than the first-stage catalyst with the amount of $Sb_2O_3$ alone changed to 0.5 to 2 parts by weight in the composition of the first-stage catalyst. The catalyst layer may be divided into two or more layers according to the amount of $Sb_2O_3$ included in the first-stage and second-stage catalysts.

By using such an antimony-added stacked catalyst, even under severe conditions involving an oxygen concentration of about 10% by weight and an ortho-xylene concentration of more than 80 g/NM$^3$ of the molecular oxygen-containing gas, the temperature of the hot spot in the catalyst layer can be restricted to 380° C. or below, and phthalic anhydride can be obtained stably over an extended period of time in a high yield of more than 117% by weight.

The following non-limitative Examples specifically illustrate the present invention.

EXAMPLE 1

Ilmenite was mixed with 80% sulfuric acid and well reacted. The reaction mixture was diluted with water to form an aqueous solution containing titanium sulfate. Iron flakes were added as a reducing agent to the aqueous solution to reduce the iron in the ilmenite to a ferrous ion. The solution was then cooled to precipitate it as ferrous sulfate. Steam heated at 150° C. was blown into the resulting aqueous solution of titanium sulfate to precipitate titanium hydroxide. It was washed with water, an acid and again with water, and calcined at 800° C. for 4 hours while passing air. The calcined product was pulverized using a jet stream to afford porous anatase-type $TiO_2$ having an average particle diameter of about 0.5 micron and a specific surface area, determined by the BET method, of 22 m$^2$/g.

Oxalic acid (200 g) was dissolved in 6400 cc of deionized water to form an aqueous solution of oxalic acid, and to the solution were added 42.73 g of ammonium metavanadate, 5.98 g of monobasic ammonium phosphate, 18.79 g of niobium chloride, 7.11 g of cesium sulfate and 36.94 g of antimony trioxide. The mixture was fully stirred. To the resulting solution was added 1800 g of $TiO_2$ obtained as above, and the mixture was stirred by an emulsifying machine to form a catalyst slurry.

A self-bonded SiC (2000 cc) having a porosity of 35% and a diameter of 5 mm was put into a stainless steel rotary furnace adapted to be heated externally and having a diameter of 35 cm and a length of 80 cm, and pre-heated to 200° to 250° C. While the furnace was rotated, the catalyst slurry was sprayed onto the SiC to support the catalyst components in an amount of 8.0 g/100 cc of the carrier. The supported product was calcined at 580° C. for 6 hours in an electrical furnace while passing air through it.

The supported material of the resulting catalyst had the following composition.

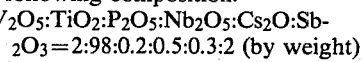
$V_2O_5$:$TiO_2$:$P_2O_5$:$Nb_2O_5$:$Cs_2O$:$Sb_2O_3$ = 2:98:0.2:0.5:0.3:2 (by weight)

The pore size distribution of the prepared catalyst was measured by a mercury penetration-type porosimeter. It was found that the pore volume of pores having a diameter of 0.15 to 0.45 micron was 86% of the pore volume of pores having a diameter of 10 microns or below (this will be referred to abbreviatedly as "the pore volume of 0.15–0.45 micron pores is 86"). The resulting catalyst was used as a first-stage catalyst.

Separately, a second-stage catalyst was prepared in the same way as above except that the amount of monobasic ammonium phosphate was changed to 17.94 g. The supported material of the resulting catalyst had the following composition.

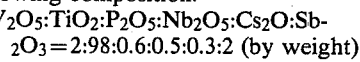
$V_2O_5$:$TiO_2$:$P_2O_5$:$Nb_2O_5$:$Cs_2O$:$Sb_2O_3$ = 2:98:0.6:0.5:0.3:2 (by weight)

The pore volume of 0.15–0.45 micron pores was 87%.

In an iron reaction tube having an inside diameter of 20 mm and a length of 3 meters dipped in a molten salt bath kept at a temperature (abbreviated N.T.) of 365° C., the second-stage catalyst was packed to a height of 1.25 meters, and then the first-stage catalyst was packed to a height of 1.25 meters. A gas prepared by mixing a synthesis gas composed of 10% by volume of oxygen, 10% by volume of water and 80% by volume of nitrogen with 83 g/NM$^3$, based on the synthesis gas, of o-xylene was passed through the reaction tube from its top at a space velocity (abbreviated S.V.) of 2500 hr$^{-1}$ (STP) to oxidize ortho-xylene catalytically. In the initial stage, phthalic anhydride was obtained in a yield of 113.4% by weight. After a lapse of about 380 days, the optimum N.T. was stable at 353° C., and the yield of phthalic anhydride somewhat increased to 113.7% by weight.

EXAMPLE 2 AND COMPARATIVE EXAMPLE

To evaluate the heat durability of a catalyst in a short period, a thermal degradation test method was employed.

The thermal degradation test method denotes a method which comprises packing the catalyst into a reaction tube and catalytically oxidizing o-xylene or naphthalene for a relatively long period of time with a gas containing molecular oxygen at a temperature higher than the optimum N.T. Since in this method, excessive oxidation becomes vigorous, the temperature of the hot spot of the catalyst naturally becomes extremely high. When the catalyst is exposed to such a severe condition for a long period of time, the heat generation at the hot spot gradually decreases as the catalyst is degraded. The heat stability of the catalyst is estimated from the speed of its degradation.

In the present Comparative Example, the thermal degradation test was performed such that the reaction was carried out using each of the following two catalysts while controlling N.T. so as to maintain the temperature of the hot spot at 550° C.

(Catalysts A)

Two catalysts were prepared in the same way as in the preparation of the first-stage and second-stage catalysts described in Example 1 except that a self-bonded SiC having a diameter of 3 mm and a porosity of 35% was used as the carrier. The amount of the catalyst components supported was 7 g/100 cc of carrier in each of these catalysts.

First-Stage catalyst (A-1)
$V_2O_5:TiO_2:P_2O_5:Nb_2O_5:Cs_2O:Sb_2O_3 = 2:98:0.2:0.5:0.3:2$ (by weight)
Pore volume of 0.15–0.45 micron pores = 86%

Second-stage catalyst (A-2)
$V_2O_5:TiO_2:P_2O_5:Nb_2O_5:Cs_2O:Sb_2O_3 = 2:98:0.6:0.5:0.3:2$ (by weight)
Pore volume of 0.15–0.45 micron pores = 86%

(Catalysts B)

Catalysts shown in B-1 and B-2 below and not containing antimony were prepared substantially in accordance with the method described in Example 1 except that a self-bonded SiC having a diameter of 3 mm and a porosity of 35% was used, the amount of the catalyst components supported was 7 g/100 cc of carrier, and the calcination was performed in an electrical furnace at 550° C. for 6 hours while passing air through it.

First-stage catalyst (B-1)
$V_2O_5:TiO_2:Nb_2O_5:Cs_2O:P_2O_5 = 4:96:0.5:0.3:0.3$ (by weight)
Pore volume of 0.15–0.45 micron pores = 87%

Second-stage catalyst (B-2)
$V_2O_5:TiO_2:Nb_2O_5:Cs_2O:P_2O_5 = 4:96:0.5:0.3:0.6$ (by weight)
Pore volume of 0.15–0.45 micron pores = 86%

In one portion of a U-shaped reaction tube having an inside diameter of 20 mm and a length of 50 cm, the first-stage catalyst (A-1) was packed to a height of 20 cm and then the second-stage catalyst (A-2) was packed to a height of 20 cm. The reaction tube was dipped in a molten salt bath. A gas prepared by mixing a synthesis gas composed of 10% by volume of oxygen, 10% by volume of water and 80% by volume of nitrogen with 85 g/NM$^3$, based on the synthesis gas, of o-xylene was passed through the reaction tube at an S.V. of 2500 hr$^{-1}$ from the other portion of the tube. In the initial stage, the optimum N.T. was 365° C., and the maximum temperature of the catalyst layer was 435° C. In the thermal degradation test, the reaction was continued by increasing N.T. to 380° C. In order to maintain the maximum temperature of the catalyst layer at 550° C. during the thermal degradation test period of 700 hours, it was necessary only to raise the N.T. to 390° C., an increase of 10° C. from the initial N.T. After the thermal degradation test, the optimum N.T. of the catalyst was 362° C. which rather showed a decrease of 3° C. from the initial N.T.

The catalysts-B were also subjected to the thermal degradation test by the same method as in the case of the catalysts-A. The optimum N.T. in the initial stage was 360° C., and the maximum temperature of the catalyst layer was about 440° C. In the thermal degradation test, the reaction was continued by increasing N.T. to 380° C. It was found that in order to maintain the maximum temperature of the catalyst layer at 550° C. during the thermal degradation test period of 700 hours, it was necessary finally to raise N.T. to 410° C. After the 700-hour thermal degradation test, the optimum N.T. of the catalysts-B rose to 378° C.

EXAMPLES 3 TO 5

The various catalysts shown below were prepared in the same way as in Example 1, and examined for variations in catalytic activity for 6 months.

TABLE 1

| Example | | Composition of the catalyst (weight ratio) | Carrier | TiO$_2$ | Pore volume of 0.15–0.45 micron pores (%) |
|---|---|---|---|---|---|
| 3 | First-stage | $V_2O_5:TiO_2:Nb_2O_5:P_2O_5:K_2O:Sb_2O_3$ = 4:96:0.8:0.3:0.18:1.5 | 5 mmφ SiC molded article (A) | 0.5μ 22m$^2$/g | 85 |
| | Second-stage | $V_2O_5:TiO_2:Nb_2O_5:P_2O_5:Rb_2O:Sb_2O_3$ = 2:98:0.15:0.8:0.3:2.5 | 5 mmφ SiC molded article (A) | 0.5μ 22m$^2$/g | 87 |
| 4 | First-stage | $V_2O_5:TiO_2:Nb_2O_5:P_2O_5:Tl_2O:Sb_2O_3$ = 10:90:0.4:0.25:0.45:4 | 5 mmφ SiC molded article | 0.6μ 15m$^2$/g | 82 |

TABLE 1-continued (catalyst)

| Example | | Composition of the catalyst (weight ratio) | Carrier | TiO$_2$ | Pore volume of 0.15–0.45 micron pores (%) |
|---|---|---|---|---|---|
| | Second-stage | V$_2$O$_5$:TiO$_2$:Nb$_2$O$_5$:P$_2$O$_5$:Cs$_2$O:Sb$_2$O$_3$ = 5:95:0.2:1.0:0.50:1 | (B) 5 mm$\phi$ SiC molded article | 0.5 22m$^2$/g | 85 |
| 5 | First-stage | V$_2$O$_5$:TiO$_2$:Nb$_2$O$_5$:P$_2$O$_5$:Cs$_2$O:K$_2$O:Sb$_2$O$_3$ = 15:85:0.6:0.35:0.10:0.15:2 | (B) 5 mm$\phi$ SiC self-bonded | 0.45$\mu$ 33m$^2$/g | 80 |
| | Second-stage | V$_2$O$_5$:TiO$_2$:Nb$_2$O$_5$:P$_2$O$_5$:Rb$_2$O:K$_2$O:Sb$_2$O$_3$ = 10:90:0.5:0.9:0.20:0.15:2 | 5 mm$\phi$ SiC self-bonded | 0.45$\mu$ 33m$^2$/g | 81 |

TABLE 2

(carrier)

| Carrier | SiC content (%) | Al$_2$O$_3$ content (%) | Apparent porosity |
|---|---|---|---|
| Molded article of SiC with a diameter of 5 mm (A) | 84 | 3 | 42 |
| Molded article of SiC with a diameter of 5 mm (B) | 81 | 8 | 36 |
| Self-bonded SiC with a diameter of 5 mm | 98 | — | 35 |

TABLE 3

(Results of reaction)

| Example | Diameter of the reaction tube (mm) | Height of the catalyst packed (mm) First-stage | Height of the catalyst packed (mm) Second-stage | Composition of the reaction gas Oxygen (vol. %) | Water (vol. %) | o-xylene (g/NM$^3$) | Naphthalene (g/NM$^3$) | Nitrogen | SV (h$^{-1}$) | Yield of phthalic anhydride (wt. %) Initial stage [N.T.]* | Three months later [N.R.]* | Six months later [N.T.]* |
|---|---|---|---|---|---|---|---|---|---|---|---|---|
| 3 | 20 | 1500 | 1500 | 10 | 10 | 100 | — | Balance | 2500 | 112.6 [363] | 112.7 [359] | 112.7 [357] |
| 4 | 20 | 1000 | 1500 | 10 | 10 | 100 | — | Balance | 2800 | 112.3 [375] | 112.6 [370] | 112.8 [367] |
| 5 | 20 | 1250 | 1250 | 10 | 10 | — | 80 | Balance | 2500 | 102.1 [368] | 102.5 [364] | 102.5 [361] |

*[N.T.] shows the variations of the temperature of the molten salt bath in the initial stage, 3 months later, and 6 months later.

EXAMPLE 6

The following two catalysts were prepared in accordance with Example 1 using porous anatase-type TiO$_2$ having an average particle diameter of 0.5 micron and a specific surface area of 22 m$^2$/g and self-bonded SiC having a diameter of 5 mm and a porosity of 35% as a carrier.

| Catalyst composition (by weight) | Amount supported (g/100cc of carrier) | Pore volume of 0.15–0.45 micron pores (%) |
|---|---|---|
| First-stage catalyst V$_2$O$_5$:TiO$_2$:P$_2$O$_5$:Nb$_2$O$_5$: Cs$_2$O:K$_2$O:Sb$_2$O$_3$ = 2:98:0.2:0.3:0.15:0.1:2 | 8.0 | 87 |
| Second-stage catalyst V$_2$O$_5$:TiO$_2$:P$_2$O$_5$:Nb$_2$O$_5$: Cs$_2$O:K$_2$O:Sb$_2$O$_3$ = 2:98:0.8:0.3:0.15:0.15:2 | 8.0 | 87 |

In a multitube heat exchange-type reactor consisting of 250 iron tubes each having an inside diameter of 20 mm and a length of 3 m, the second-stage catalyst was packed to a height of 1.3 m, and then the first-stage catalyst was stacked to a height of 1.3 m. A molten salt was used as a heat transfer medium, and circulated through the reactor to maintain the temperature at 367° C.

From the top of the reactor, a gaseous mixture of o-xylene and air was passed at an S.V. of 2500 hr$^{-1}$ and the concentration of o-xylene was maintained at 40 g/NM$^3$ of air. Then, the reaction product gas was cooled and the reaction product was collected. By operating a blower, a part of the waste gas was recycled to the reactor. When the concentration of oxygen in the starting gas at the inlet of the reactor reached 11% by volume, the amount of o-xylene fed was gradually increased so that finally the concentration of o-xylene reached 100 g/NM$^3$ of the molecular oxygen-containing gas. The amount of the waste gas recycled was automatically controlled according to an increase in the amount of o-xylene fed so that the concentration of oxygen in the starting gas was maintained at 11% by volume.

The gas which left the reactor was cooled to 160° C. by a heat exchanger, and introduced into a switchtype collecting chamber where the resulting phthalic anhydride was cooled and collected. Since the concentration of phthalic anhydride in the product gas was high, about 33% of the total amount of phthalic anhydride collected was in the liquid state.

The waste gas left the collecting chamber at 77° C. It was passed through a conduit kept at 120° to 130° C., and 51.6% of the waste gas was recycled as a starting gas which was fed to the reactor together with air and o-xylene.

The remaining 48.4% of the waste gas was introduced into a catalytic combustion device, completely burnt, and then released into the atmosphere.

Under these conditions, the concentration of steam in the inlet gas of the reactor was about 8.7% by volume. During the long-term operation for about 6 months, the results of the reaction were as shown in Table 4.

TABLE 4

(Results of reaction)

| | N.T. (°C.) | S.V. ($hr^{-1}$) | Concentration of o-xylene (g/$NM^3$) | Yield of phthalic anhydride (wt. %) | $\Delta T_1$* (°C.) | $\Delta T_2$** (°C.) |
|---|---|---|---|---|---|---|
| Initial stage | 367 | 2500 | 100 | 113.1 | 74 | 24 |
| 2 months later | 362 | 2500 | 100 | 113.5 | 72 | 21 |
| 4 months later | 358 | 2500 | 100 | 113.5 | 71 | 21 |
| 6 months later | 357 | 2500 | 100 | 113.4 | 69 | 22 |

*Difference between N.T. with the first-stage catalyst and the maximum temperature of the catalyst layer.
**Difference between N.T. with the second-stage catalyst and the maximum temperature of the catalyst layer.

EXAMPLES 7 AND 8

The catalysts shown in Table 5 were prepared in the same way as in Example 1 except that self-bonded SiC having a diameter of 4 mm and a porosity of 35% was used as the carrier, and examined for variations in catalytic activity for 6 months. The results are shown in Table 6.

TABLE 5

(catalyst)

| Example | Composition of the catalyst (weight ratio) | | $TiO_2$ Diameter ($\mu$) | $TiO_2$ Specific surface area ($m^2$/g) | Pore volume of 0.15–0.45 micron pores (%) | Amount supported (g/100 cc of carrier) | Calcining temperatures (°C.) |
|---|---|---|---|---|---|---|---|
| 7 | First-stage | $V_2O_5:TiO_2:Nb_2O_5:P_2O_5:Cs_2O:Sb_2O_3$ = 3:97:0.5:0.2:0.4:2.5 | 0.5 | 20 | 85 | 30 | 500 |
| | Second-stage | $V_2O_5:TiO_2:Nb_2O_5:P_2O_5:Cs_2O:Sb_2O_3$ = 3:97:0.5:0.2:0.4:1.0 | " | " | 87 | 30 | " |
| 8 | First-stage | $V_2O_5:TiO_2:Nb_2O_5:P_2O_5:Tl_2O:K_2O:Sb_2O_3$ = 10:90:0.8:0.5:0.3:0.2:6.0 | " | 34 | 80 | 100 | " |
| | Second-stage | $V_2O_5:TiO_2:Nb_2O_5:P_2O_5:K_2O:Rb_2O:Sb_2O_3$ = 10:90:0.4:1.0:0.1:0.2:1.5 | " | " | 82 | 100 | " |

TABLE 6

(Results of reaction)

| Example | Diameter of the reaction tube (mm) | Heights of the catalyst packed (mm) First-stage | Heights of the catalyst packed (mm) Second-stage | Composition of the reaction gas Oxygen (vol. %) | Composition of the reaction gas Water (vol. %) | Composition of the reaction gas o-xylene (g/$NM^3$) | Composition of the reaction gas Nitrogen | SV ($h^{-1}$) | Yield of phthalic anhydride (wt. %) Initial stage [N.T.]* | Yield of phthalic anhydride (wt. %) Three months later [N.T.]* | Yield of phthalic anhydride (wt. %) Six months later [N.T.]* |
|---|---|---|---|---|---|---|---|---|---|---|---|
| 7 | 20 | 1500 | 1500 | 10 | 10 | 90 | Balance | 2000 | 118.5 [313] | 118.7 [310] | 118.8 [310] |
| 8 | 20 | 1500 | 1500 | 10 | 10 | 90 | Balance | 2000 | 117.1 [275] | 117.4 [273] | 117.6 [272] |

*[N.T.] shows the variations of the temperature of the molten salt bath in the initial stage, 3 months later, and 6 months later.

EXAMPLE 9

Oxalic acid (250 g) was dissolved in 2000 cc of deionized water to form an aqueous solution of oxalic acid. Ammonium meta-vanadate (117 g) was dissolved in the resulting aqueous solution. To the resulting aqueous solution was added 146 g of antimony trioxide, and they were fully mixed. The mixture was evaporated to dryness, and then calcined at 700° C. to form a solid product.

X-ray diffraction analysis of the solid product showed that there was a main peak at $2\theta = 27.4°$. By the Inorganic Index of the Powder Diffraction File (1970), page 716, this product was identified as antimony vanadate ($SbVO_4$).

Monobasic ammonium phosphate (6.02 g), 18.86 g of nioibium chloride and 7.15 g of cesium sulfate were added to 6400 cc of deionized water, and they were fully stirred. To the solution were added 144.97 g of antimony vanadate obtained as above and 1800 g of the same $TiO_2$ as obtained by the method of Example 1, and they were stirred by an emulsifying machine to prepare a catalyst slurry.

2000 cc of self-bonded SiC having a diameter of 3 mm and a porosity of 35% was put into a stainless steel rotary furnace adapted to be heated externally, and the above catalyst slurry was sprayed onto the carrier to support the catalytically active material at a rate of 50 g/100 cc of carrier. The supported product was then calcined at 500° C. for 3 hours in an electrical furnace while passing air through it. The composition of the supported material in the resulting catalyst was as follows:

$V_2O_5:TiO_2:Nb_2O_5:P_2O_5:Cs_2O:Sb_2O_3 = 3:97:0.5:0.2:0.3:4.8$ (by weight).

The pore volume of 0.01–0.45 micron pores of the prepared catalyst was 84%. This catalyst was used as a first-stage catalyst.

Separately, 140 g of oxalic acid was dissolved in 6400 cc of deionized water to form an aqueous solution of oxalic acid. To the solution were added 56.68 g of ammonium metavanadate, 12.04 g of monobasic ammonium phosphate, 18.86 g of niobium chloride and 7.15 g of cesium sulfate, and they were fully dissolved. To the resulting solution were added 30.21 g of antimony vanadate used in the preparation of the first-stage catalyst above and 1800 g of the same $TiO_2$ as used in Example 1. The mixture was stirred by an emulsifying machine to form a catalyst slurry. In the same way as in the preparation of the first-stage catalyst, the catalyst slurry was sprayed onto the same carrier as above to support the catalytically active material at a rate of 50 g/100 cc of carrier. The supported product was calcined at 500° C. for 3 hours. The supported material of the resulting catalyst had the following composition.

$V_2O_5:TiO_2:Nb_2O_5:P_2O_5:Cs_2O:Sb_2O_3 = 3:97:0.5:0.4:0.3:1.0$ (by weight).

The pore volume of 0.15–0.45 micron pores of the resulting catalyst was 85%. This catalyst was used as a second-stage catalyst.

In an iron reaction tube having an inside diameter of 20 mm and a length of 3 meters and dipped in a molten salt bath maintained at 305° C., the second-stage catalyst was packed to a height of 1.2 meters, and then the first-stage catalyst was packed to a height of 1.3 meters. A gas prepared by mixing a synthesis gas composed of 10% by volume of oxygen, 10% by volume of water and 80% by volume of nitrogen with 85 g/NM³, based on the synthesis gas, of o-xylene was passed through the reaction tube from its top at an S.V. of 2,000 hr⁻¹ (STP) to oxidize the o-xylene catalytically. In the initial stage, phthalic anhydride was obtained in a yield of 117.4%. After a lapse of about 150 days, the optimum temperature of the molten salt was stable at 302° C., and the yield of phthalic anhydride was 117.8% by weight.

EXAMPLE 10

By the same method as described in Example 1, the following first-stage and second-stage catalysts were prepared. The calcining temperature was 500° C.

|  | Composition of the catalyst (weight ratio) | Pore volume of 0.15–0.45 micron pores (%) | Amount supported per 100 cc of carrier (%) |
| --- | --- | --- | --- |
| First-stage catalyst | $V_2O_5:TiO_2:Nb_2O_5:P_2O_5:Cs_2O:Sb_2O_3 = 4:96:0.5:0.3:0.3:3.5$ | 84 | 30 |
| Second-stage catalyst | $V_2O_5:TiO_2:N_2O_5:P_2O_5:K_2O:Sb_2O_3 = 3:97:0.5:0.4:0.3:1.5$ | 85 | 30 |

In an iron reaction tube having an inside diameter of 25 mm and a length of 3 meters and dipped in a molten salt bath maintained at 320° C. the second-stage catalyst was first packed to a height of 1.1 meters, and then the first-stage catalyst was packed to a height of 1.4 meters. A gaseous mixture consisting of air and 60 g/NM³, based on the air, of o-xylene was passed through the reaction tube at a space velocity (SV) of 2500 hr⁻¹ to oxidize the o-xylene catalytically. In the initial stage, the phthalic anhydride was obtained in a yield of 117.6% by weight. After a lapse of 6 months, the optimum reaction temperature was stable at 316° C., and the yield of phthalic anhydride was 117.9% by weight.

What we claim is:

1. A catalyst for the production of phthalic anhydride by the catalytic vapor-phase oxidation of o-xylene or naphthalene with molecular oxygen, said catalyst comprising a catalytically active material composed of 1 to 20 parts by weight as $V_2O_5$ of vanadium oxide and 99 to 80 parts by weight as $TiO_2$ of anatase-type titanium oxide being porous and having a particle diameter substantially of 0.4 to 0.7 micron and a specific surface area of 10 to 60 m²/g, and per 100 parts by weight of the sum of these two components, 0.01 to 1 part by weight as $Nb_2O_5$ of niobium, 0.05 to 1.2 parts by weight as oxide of potassium, cesium, rubidium or thallium, 0.2 to 1.2 parts by weight as $P_2O_5$ of phosphorus and 0.5 to 10 parts by weight as $Sb_2O_3$ of antimony, said catalytically active material being supported on a porous carrier in an amount of 3 to 200 g/100 cc of carrier.

2. The catalyst of claim 1 wherein a layer of the catalytically active material supported on the porous carrier is characterized by the fact that the pore volume of its pores having a diameter of 0.15 to 0.45 is at least 50% of the pore volume of its pores having a diameter of not more than 10 microns.

3. The catalyst of claim 1 wherein the porous carrier has an alumina content of not more than 10% by weight, and a silicon carbide content of at least 80% by weight.

4. The catalyst of claim 1 wherein the porous carrier has an alumina content of not more than 5% by weight, a silicon carbide content of at least 95% by weight, and an apparent porosity of 15 to 40%.

5. The catalyst of claim 1 wherein the anatase-type titanium oxide has a particle diameter substantially of 0.45 to 0.60 micron and a specific surface area of 15 to 40 m²/g.

* * * * *

UNITED STATES PATENT AND TRADEMARK OFFICE
CERTIFICATE OF CORRECTION

PATENT NO. : 4,356,112
DATED     : October 26, 1982
INVENTOR(S) : Yoshiyuki Nakanishi et al It is certified that error appears in the above-identified patent and that said Letters Patent is hereby corrected as shown below:

ON THE TITLE PAGE, Assignee should read

-- Nippon Shokubai Kagaku Kogyo Co., Ltd., Osaka, Japan --.

Signed and Sealed this

First Day of March 1983

[SEAL]

Attest:

GERALD J. MOSSINGHOFF

Attesting Officer  Commissioner of Patents and Trademarks